US010123823B2

(12) United States Patent
El Chaar

(10) Patent No.: US 10,123,823 B2
(45) Date of Patent: Nov. 13, 2018

(54) SYSTEM AND METHOD FOR DENTAL IMPLANT SURGERY

(76) Inventor: Edgard El Chaar, New York, NY (US)

( * ) Notice: Subject to any disclaimer, the term of this patent is extended or adjusted under 35 U.S.C. 154(b) by 713 days.

(21) Appl. No.: 13/117,433

(22) Filed: May 27, 2011

(65) Prior Publication Data

US 2011/0294092 A1 Dec. 1, 2011

Related U.S. Application Data

(60) Provisional application No. 61/349,545, filed on May 28, 2010, provisional application No. 61/364,461, filed on Jul. 15, 2010.

(51) Int. Cl.
| | |
|---|---|
| *A61B 17/56* | (2006.01) |
| *A61B 17/32* | (2006.01) |
| *A61C 3/03* | (2006.01) |
| *A61C 8/00* | (2006.01) |

(52) U.S. Cl.
CPC ............ *A61B 17/56* (2013.01); *A61B 17/32* (2013.01); *A61B 17/320068* (2013.01); *A61C 3/03* (2013.01); *A61C 8/0089* (2013.01); *A61C 8/0092* (2013.01); *A61B 2017/564* (2013.01)

(58) Field of Classification Search
CPC . A61B 17/32; A61B 17/320068; A61B 17/56; A61B 2017/564; A61C 3/03; A61C 8/0089; A61C 8/0092

USPC ............... 433/140–141, 144–145, 172–174; 606/79–80, 84, 86 R

See application file for complete search history.

(56) References Cited

U.S. PATENT DOCUMENTS

| | | | |
|---|---|---|---|
| 6,799,970 B2* | 10/2004 | Martin et al. ................. | 433/173 |
| 8,002,548 B2* | 8/2011 | Lee ................................ | 433/173 |
| 8,080,012 B2* | 12/2011 | Chen ........................... | 606/86 R |
| 2006/0204929 A1* | 9/2006 | Kitamura et al. ............ | 433/173 |
| 2007/0015102 A1 | 1/2007 | Vercellotti et al. | |
| 2008/0161934 A1* | 7/2008 | Yamada ..................... | 623/17.17 |
| 2009/0004624 A1* | 1/2009 | Lee ................................ | 433/144 |
| 2009/0024118 A1 | 1/2009 | Vercellotti et al. | |
| 2009/0136894 A1 | 5/2009 | Tomaso et al. | |
| 2010/0167235 A1 | 7/2010 | Vercellotti et al. | |

* cited by examiner

*Primary Examiner* — Larry E Waggle, Jr.
(74) *Attorney, Agent, or Firm* — Sofer & Haroun, LLP

(57) ABSTRACT

A method for performing an inferior lift in the sinus includes preparing an initial opening in the bone that is drilled to a depth just prior to reaching a sinus floor. Using a sonic drilling device, a final portion of the sinus floor is removed until a schneiderian membrane is reached. A bone graft is inserted into the opening, lifting said schneiderian membrane. After ossification of the bone graft, an implant is inserted into the opening and graft.

4 Claims, 10 Drawing Sheets

SYSTEM AND METHOD FOR DENTAL IMPLANT SURGERY

RELATED APPLICATION

This application claims the benefit of priority of U.S. patent application Nos. 61/349,545, filed on May 28, 2010 and 61/364,461 filed on Jul. 15, 2010, the entirety of which are incorporated by reference.

BACKGROUND

In the area of dental/periodontology implants, inferior lift technique has been used successfully for many years. In certain cases, the bone thickness in the region where the implant is to be inserted is not of ideal depth. The inferior lift technique involves drilling the bone to the floor of the sinus then breaking the floor of the sinus using osteotomes and exposing the schneiderian membrane. The membrane is then elevated and a bone graft is inserted into the opening. This bone graft eventually ossifies and provides a better thickness to properly support the dental implant.

However, there are at least two drawbacks associated with the present inferior lift technique. First, patients undergoing this procedure always describe it as an uncomfortable process due to the necessary tapping of the osteotomes against the bones involved. For example, even with proper anesthesia, an osteotome is still used to break the floor of the sinus to expose the schneiderian membrane. This tapping reverberates throughout the bone (and neighboring bones) and is uncomfortable.

Additionally, when using osteotomes, the repeated tapping on the sinus floor is somewhat imprecise and thus carries risk of rupturing the schneiderian membrane. If the schneiderian membrane is ruptured it can cause infection and otherwise delay the bone graft/lift procedure.

OBJECTS AND SUMMARY

The present technique minimizes or avoids the above described drawbacks by preparing the opening and breaking the floor of the sinus using a new combination of drill/cutting implements and technique for using the same, thus exposing the schneiderian membrane without the use of osteotomes. The membrane can then be elevated after using this technique and bone is plugged in without any of the uncomfortable tapping on the sinus and with a greatly reduced risk of rupturing the schneiderian membrane.

BRIEF DESCRIPTION OF THE DRAWINGS

The present invention can be best understood through the fallowing description and accompanying drawings, wherein.

DETAILED DESCRIPTION

The following is an exemplary description of the implant procedure described in accordance with the accompanying FIGS. 1-10.

Figure 1:
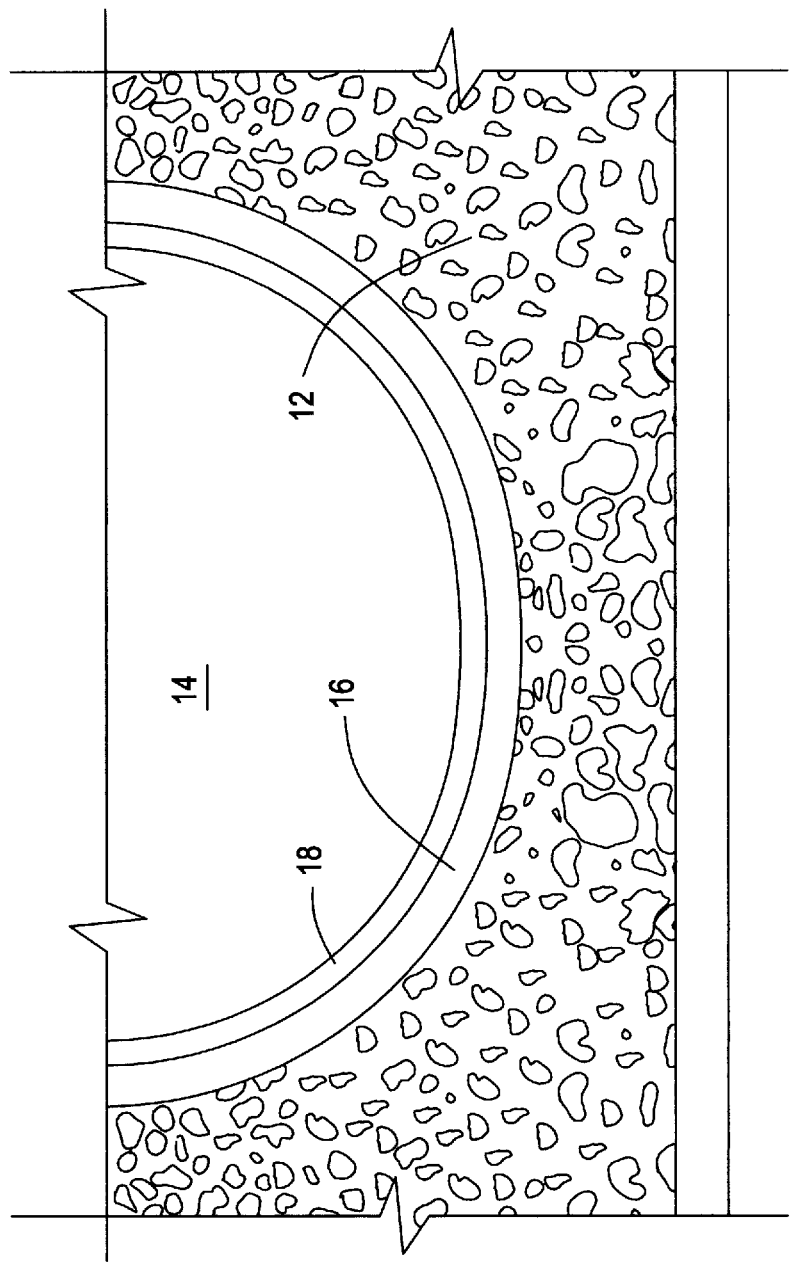
FIG. 1 is an image of the dental implant region, in accordance with one embodiment.

FIG. 1 shows generally the tooth area that undergoes an inferior lift procedure and receives a bone graft. In this figure, bone area 12 receives the intended bone graft. Open area 14 represents the sinus cavity. Hard floor 16 is the bottom portion of bone area 10 that borders the schneiderian membrane 18 which forms the bottom of sinus cavity 14.

Figure 2:
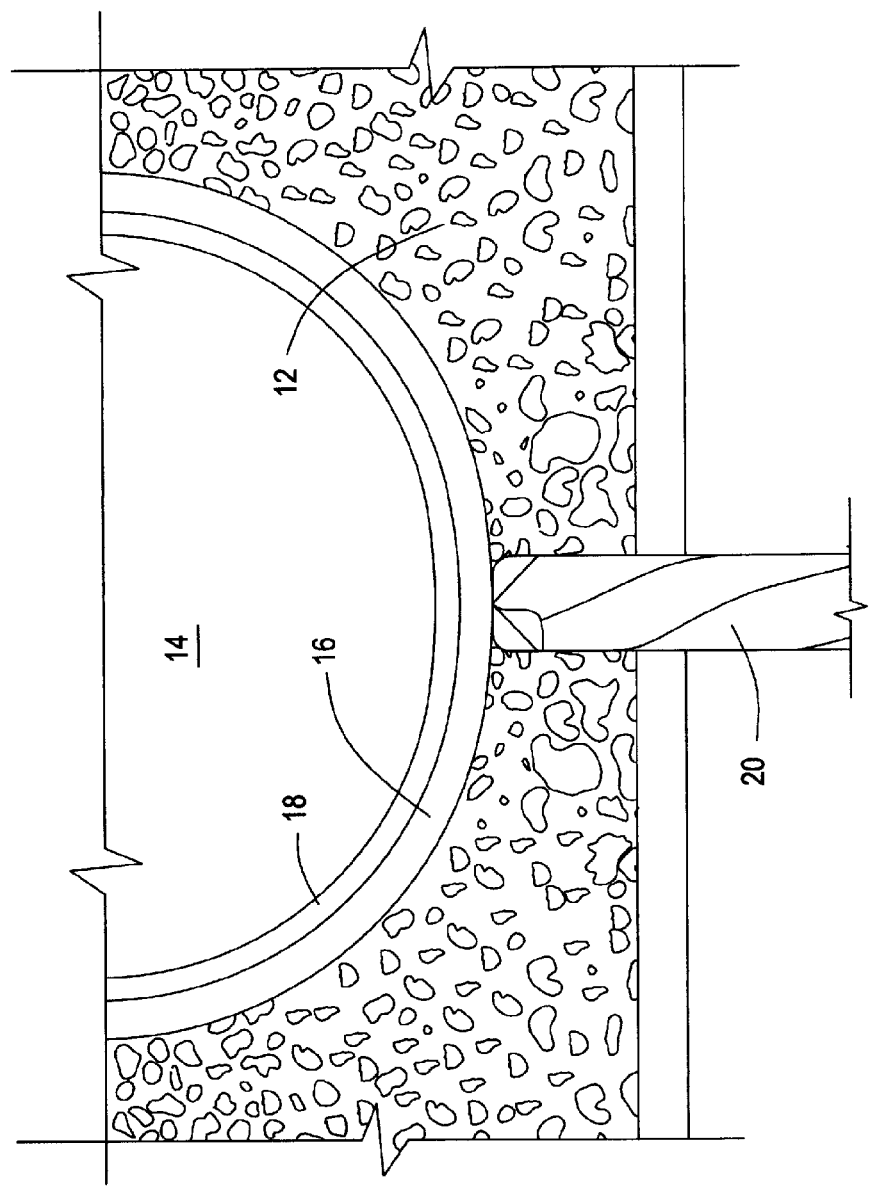
FIG. 2 is an image of a step of the process for drilling through the bone to the sinus floor, in accordance with one embodiment.

In a first step in the inferior lift procedure as shown in FIG. 2, the process begins by drilling the initial opening into the bone using a standard dental drill bit 20 of the appropriate size. Typically, drill bit 20 would be approximately 2.0 mm in diameter in accordance with the typical implant sizes, discussed in more detail below. Such a procedure mirrors the prior art procedure. Because of the nature of drill bit 20 and the available precision when using ft, the drill depth must be estimated to be short of the sinus floor. Drill bit 20 cannot be used to expose all the way to the schneiderian membrane 18 without significant risk of breaking or rupturing the membrane because it cannot be used in such a manner to have its depth controlled with precision (e.g. via tactile feedback in the user's hand). In one example, using a pilot twist drill, drill bit 20 is used for creating the opening through the majority of the bone, except for approximately the final 1 mm below maxillary sinus cavity (representing the approximate thickness of sinus floor 16 and schneiderian membrane 18).

In the prior art, the same bit may be used in multiple iterations until the hole in bone 12 is wide enough and then an osteotome is used to complete the break of sinus floor 16, since such an implement can be used with more precision than the initial drill bit 20 pictured in FIG. 2. However, as outlined above, the use of the osteotomes to complete the break of sinus floor 16 is painful for the patient.

Figure 3:
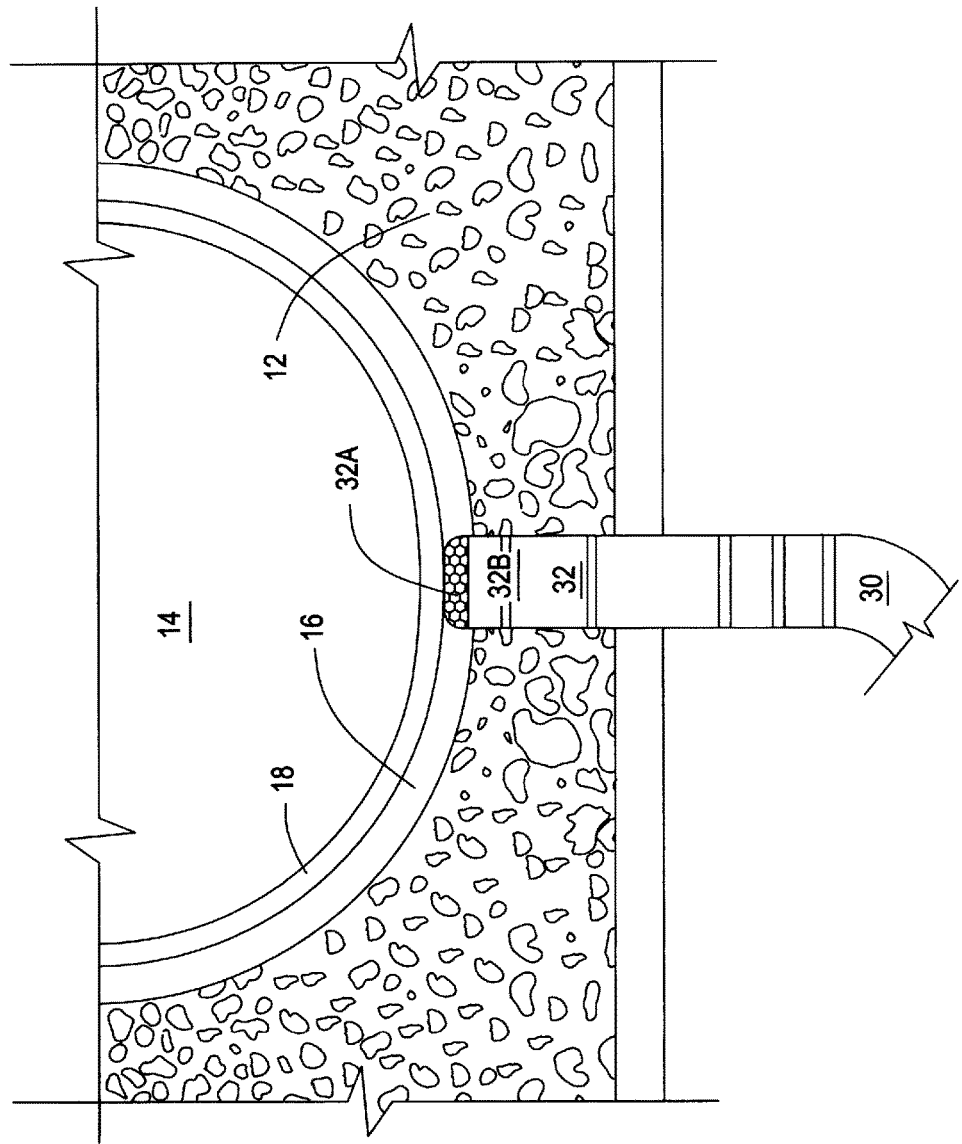
FIG. 3 is another image of a step of the process for drilling through the bone to the sinus floor, in accordance with one embodiment.

In the present arrangement, as shown in FIG. 3, instead of using an osteotome to complete the break of sinus floor 16, a sonic drilling implement 30 is used to complete the break of sinus floor 16. Sonic drilling devices, such as sonic drilling device 30, utilize variable modulation ultrasonic vibrations that are activated only when its cutting tip 32 is n contact with the bone tissue to be cut.

An exemplary sonic drilling implement 30 may be a sonic bone drill as disclosed in U.S. Patent Application No. 2009/0023118, assigned to Piezosurgery, the entirety of which is incorporated by reference.

Such "drilling devices" are advantageous because they provide a significantly more precise cutting ability on bone tissue while simultaneously providing better assurance that nearby soft tissue is not damaged since such sonic cutting tips, such as tip 12, lose their cutting capacity when contacting soft tissue (the soft tissue absorbs the sound vibrations).

In this context, using sonic drilling implement 30 with tip 32, having a diameter substantially corresponding to the initial drill bit 20 (e.g. 2.0 mm), implement 30 is used to remove the remaining 1 mm of bone (sinus floor 16 is the final portion of bone before schneiderian membrane 18 SM).

In one arrangement, tip 32 of sonic drilling implement 30 may be a specific tip 32 for such inferior lift procedure. It is noted that, in general, sonic cutting tips have an active cutting region and other non-cutting regions as well. In the present FIG. 3, region 32A represents the active region of tip 32 and region 32B represents the non-cutting portion of tip 32.

The portion 32B of tip 32 that is not active does not act to cut the neighboring bone 12 which it contacts. The only bone that is cut by tip 32 is bone that is kept in pressing contact with tip 32 via active region 32A. As shown in FIG. 3, active region 32A of the cutting tip 32 is very small and directionally only active in the forward (front) tip direction so that the only portion of bone being cut is the final 1 mm of sinus floor/bone 16.

Figure 4:
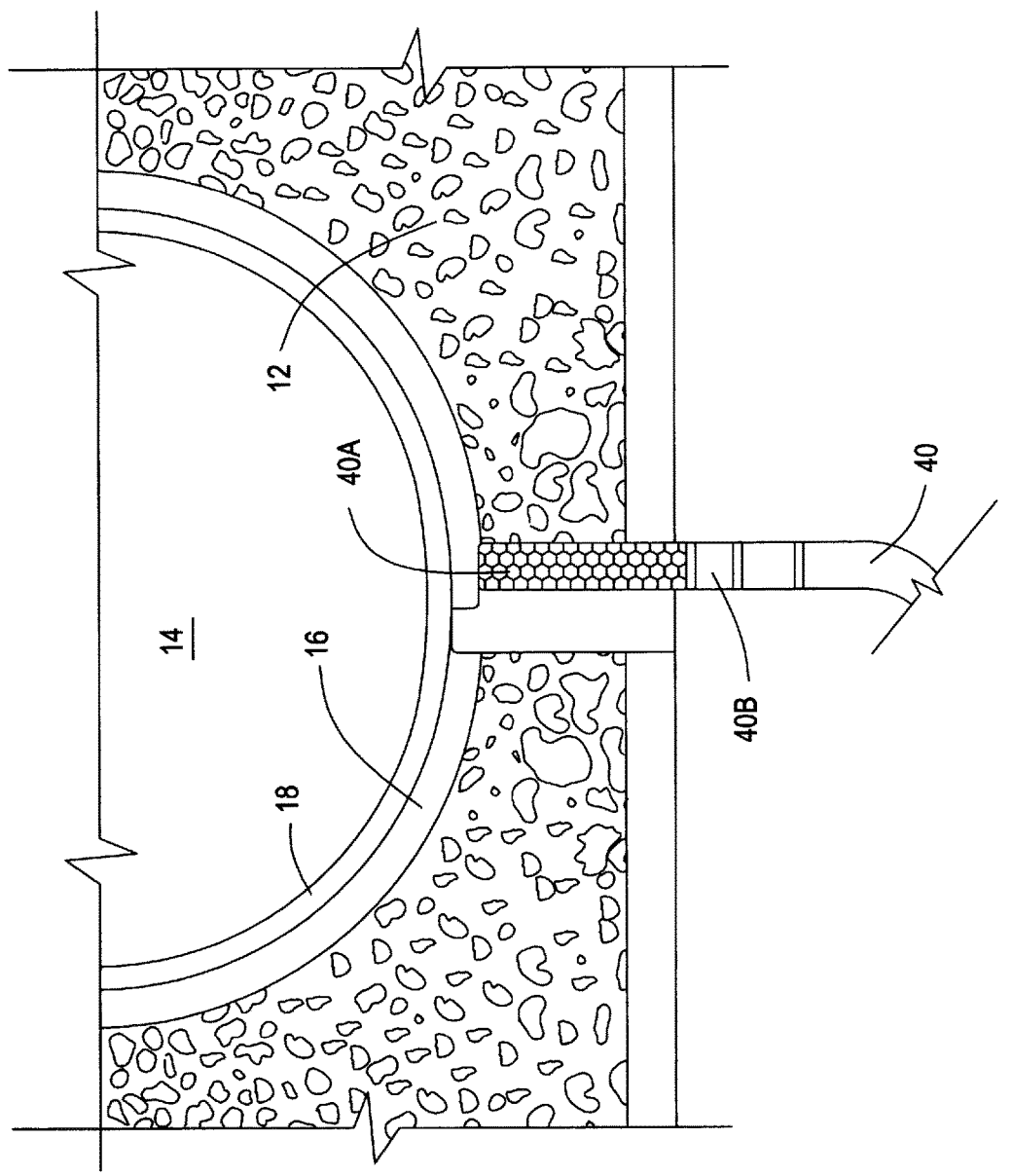
FIG. 4 is an image of a step of the process for widening of the graft opening, in accordance with one embodiment.
Figure 5:
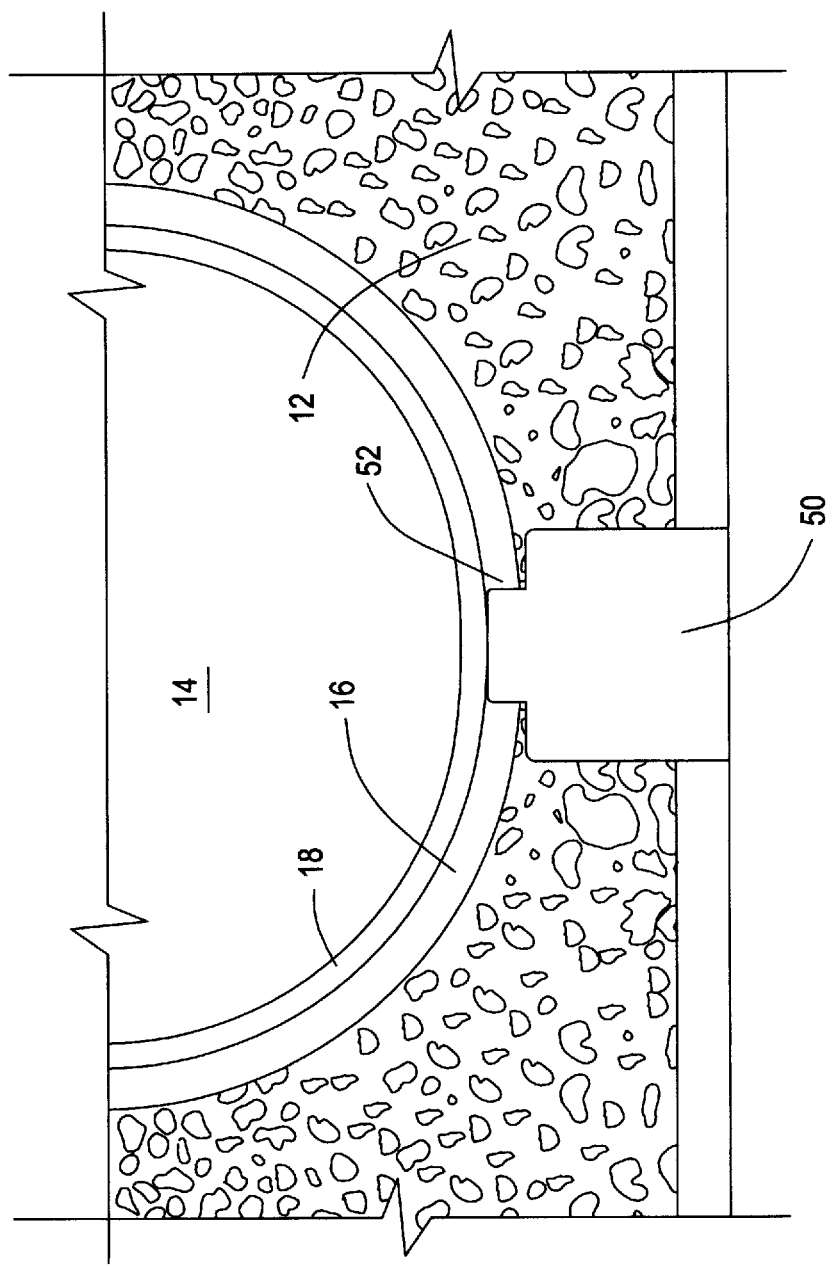
FIGS. 5-6 is an image of an intermediate stage of the drilling process in the graft opening, with FIG. 6 showing an axial view of the opening.
Figure 6:
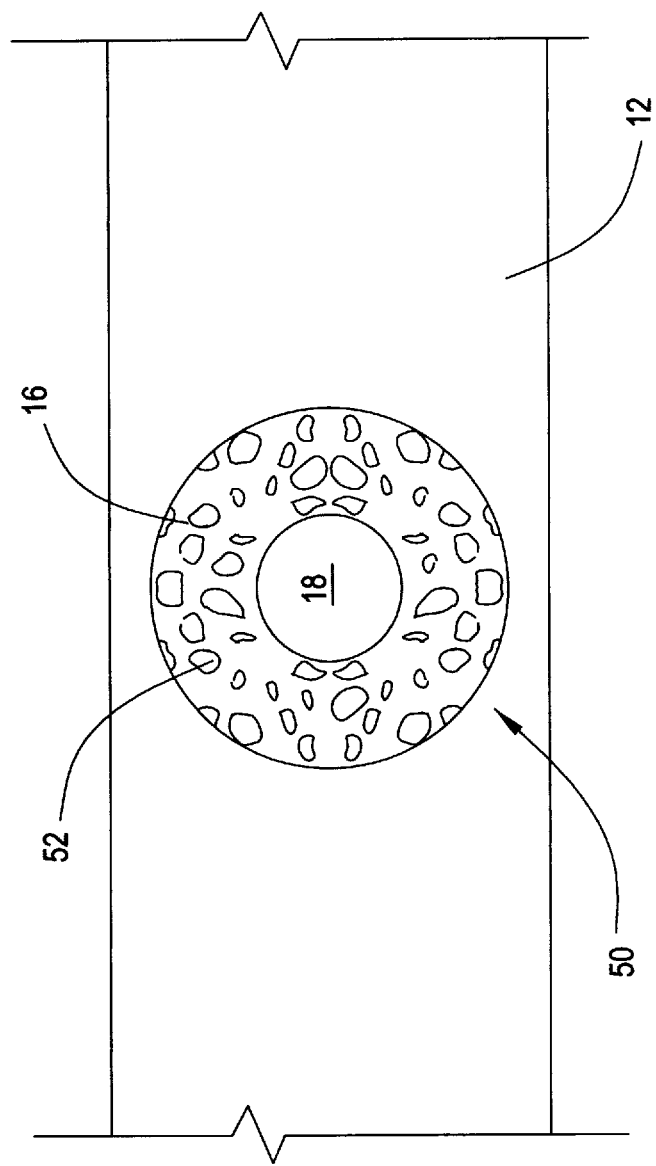

As shown in FIG. 4, Once the initial opening is made through bone 12 and completed through sinus floor 16, a different widening sonic tip 40 may be used to widen the initial opening to the desired width (i.e. with respect to the size of the desired implant). In this widening tip 40, the active area 40A is not only a front active area, but also a side active area 40B (360.degree.) to allow bone 12 to be drilled laterally. In this step the main portion of bone 12 is drilled using lateral motion exposing a greater part of sinus floor 16 until a circular opening 50 is made to its full size with only a small donut shaped area 52 of sinus floor 16 remaining. As a result, there is a small opening to membrane 18 in the center of a larger hole through bone 12 with circular or doughnut shaped ring 52 of the final 1 mm of sinus floor/bone 16. This is shown in FIGS. 5 (in cut-away) and 6 (axial view).

Figure 7:
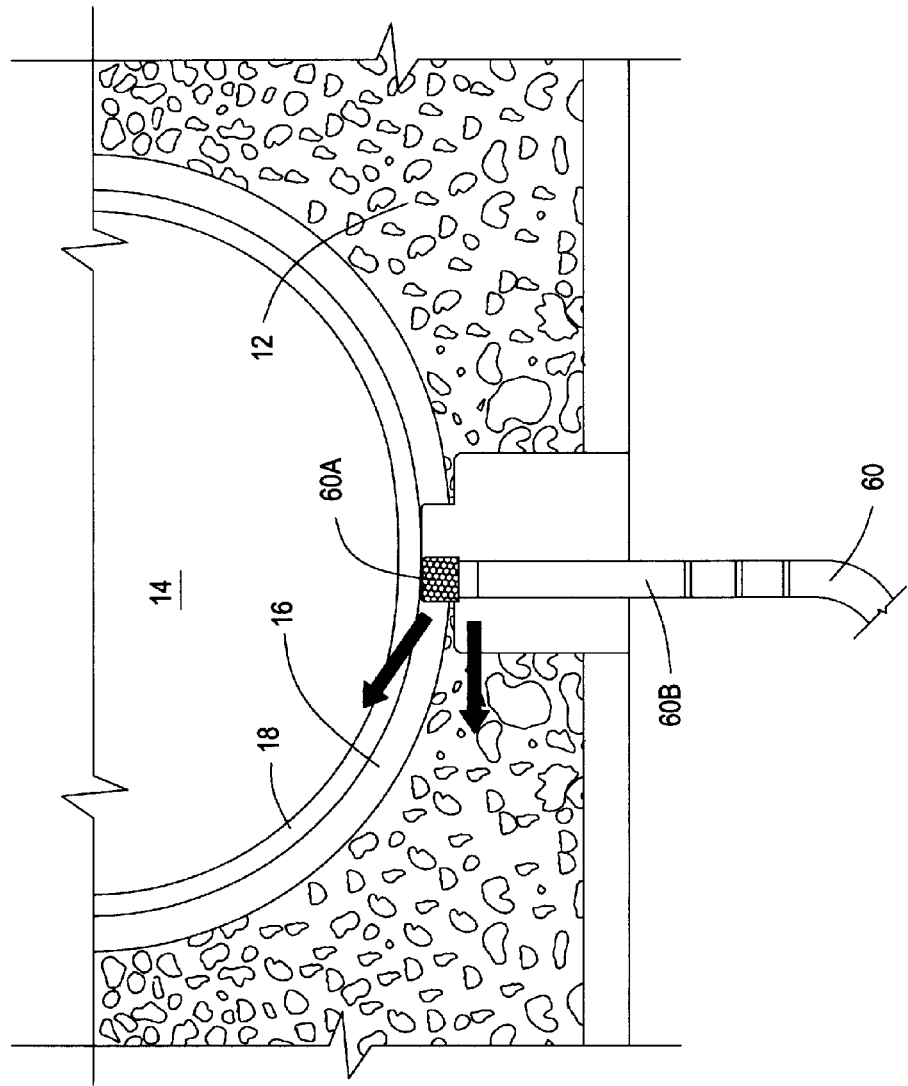
FIG. 7 is an image of a step of the process for widening of the graft opening, in accordance with one embodiment.
Figure 8:
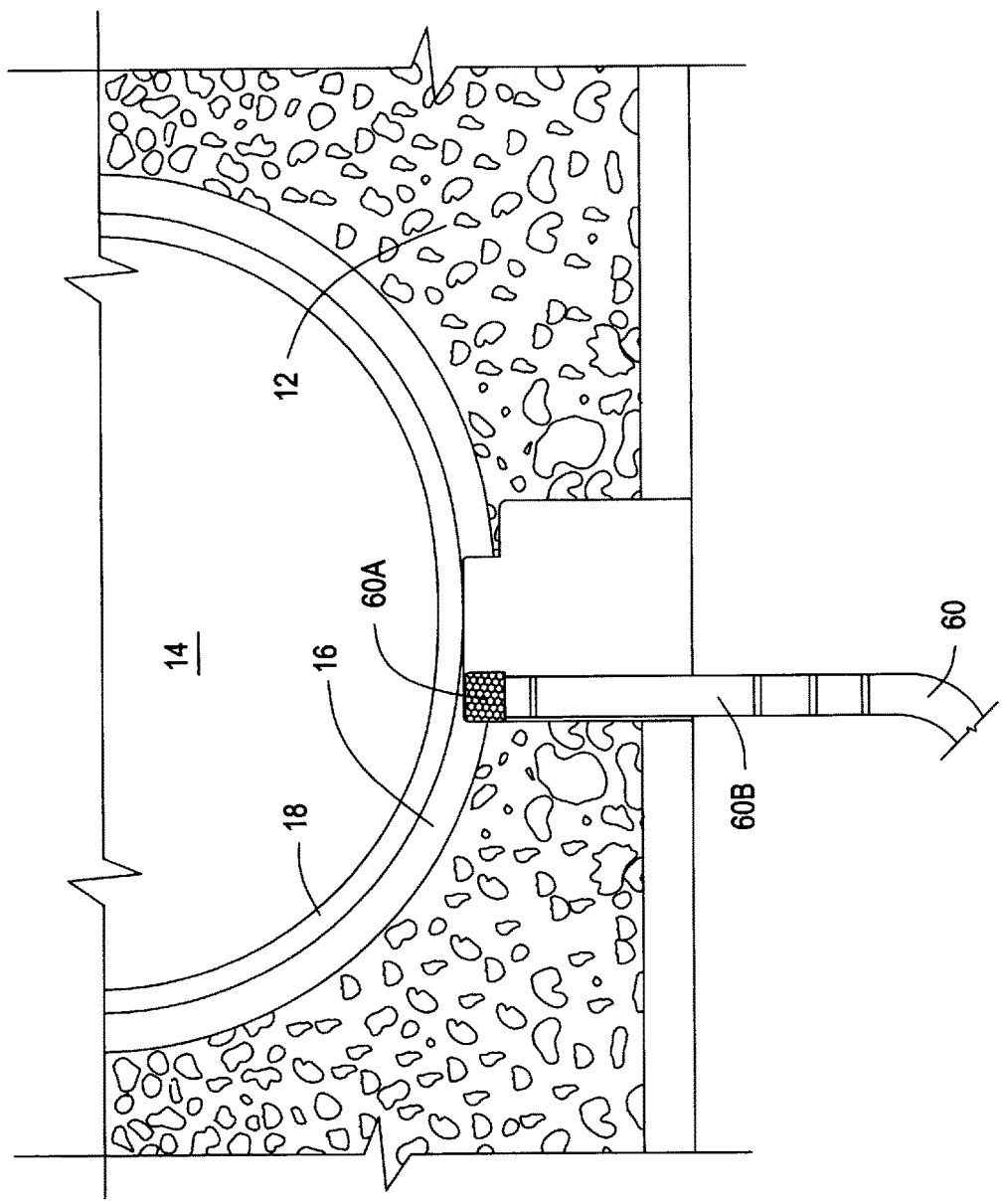
FIG. 8 is another image of a step of the process for widening of the graft opening, in accordance with one embodiment.

It is noted that each of the various bone grafts/implants that may be used have different shapes (eg, cylindrical, conical, etc. . . . ). In the next step, as shown in FIGS. 7-8, final ring 52 of sinus floor 16 bone (the doughnut shape) is removed, using a sonic cutting tip 60, preferably a specially configured tip 60, where the active area 60A only cuts in the forward direction and only slightly along the sides of the front of tip 60. Unlike tips 30 and 40, cutting tip 60 is dimensioned with a limited active area 60A (inactive area 60B) such that in operation there is no accidental bone removal along the sides of the main opening in the main portion of bone 12, which could make hole too large to accept the desired implant. Using this sonic tip 60, the desired shape of the removal of the final 1 mm of sinus floor/bone 16 can be achieved, again without the use of osteotomes and likewise without damage to schneiderian membrane 18.

In one embodiment, the size of tip 60 is dimensioned in diameter to be slightly smaller than the size of the size/diameter of the intended implant, discussed below as implant 74, so as not to inadvertently overly widen the opening which could result in a loose fit for the implant. For example, if the implant is 3.7 mm, the diameter of tip 60 may be 3.4 mm for eliminating ring 52 of sinus floor 16. Alternatively, if the implant is 4.1 mm tip 60 may be or a 3.8 mm, or if the implant is 4.7 mm then tip 60 may be 4.2 mm in diameter.

Figure 9:
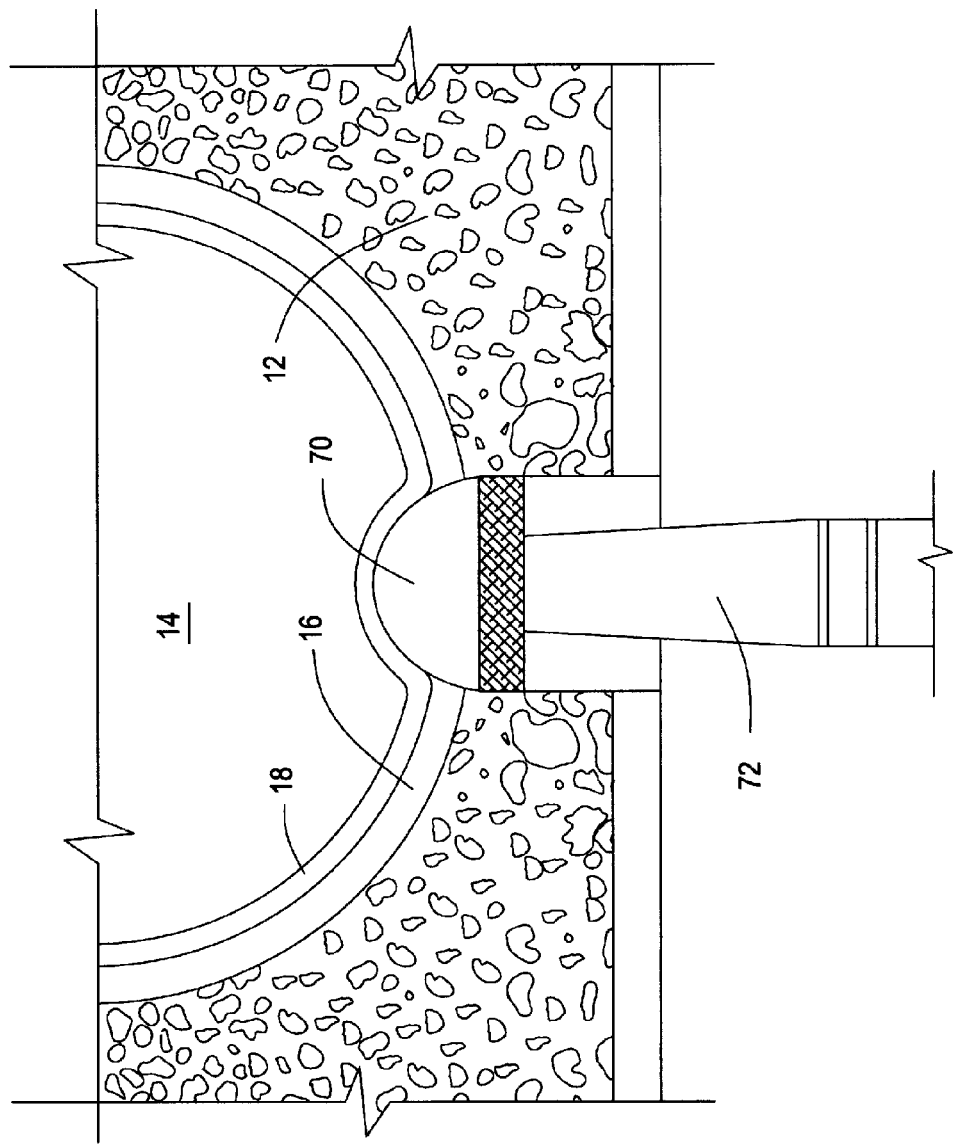
FIG. 9 is an image of a step of the process for inserting the bone graft, in accordance with one embodiment.

Once the above drilling procedures are complete, as shown in FIG. 9, a bone graft 70 is pressed into the opening using an osteotome 72 or other pressing device, lifting the floor of schneiderian membrane 18 of the sinus. It is noted that the usage of an osteotome in this respect is not the same as the use of osteotomes for breaking sinus floor 16 as in prior arrangements. Here the osteotome is being used only after the creation of the opening as per the above steps, primarily as a pressing device.

Figure 10:
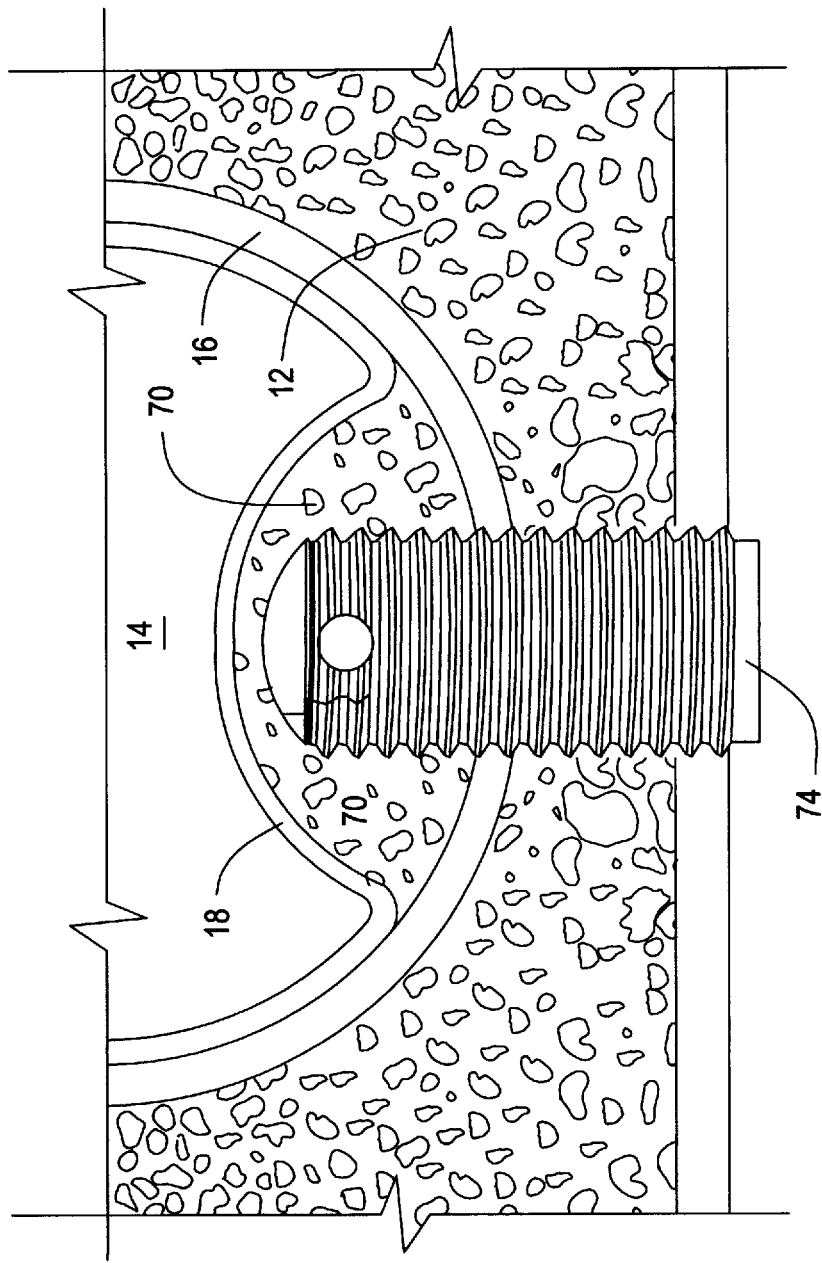
FIG. 10 is an image showing the completed graft with the implant therein, in accordance with one embodiment.

As shown in the final FIG. 10, once the opening/bone graft 70 has had a sufficient amount of time for the graft to ossify, the implant 74 may be screwed/inserted into place.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A method for performing an inferior lift in a sinus, said method comprising the steps of:

preparing an initial opening in a bone including a marrow section and a hard sinus floor, said initial opening being drilled through said marrow section to a depth just prior to reaching said hard floor of said sinus;

removing a portion of said hard sinus floor, located within said initial opening until a schneiderian membrane is reached, exposing said schneiderian membrane, said removal using a sonic drilling device with a first tip that has an active portion that is substantially limited to a front region of said first tip said first tip configured to remove bone only in a forward direction of said first tip without substantially cutting contact with said marrow section of said bone;

removing any remaining doughnut shaped hard floor of said sinus using a second tip on said sonic drilling device that has an active portion that is substantially limited to 360 degrees about a circumference of a forward end of said second tip, said second tip configured to remove bone substantially in a lateral direction of said second tip without substantial cutting contact with said marrow section of said bone and clearing a widened opening in said hard sinus floor of said bone, but retaining a narrower hole through said hard floor of said sinus;

inserting a bone graft into said widened opening, lifting said schneiderian membrane; and after ossification of said bone graft, inserting an implant into said widened opening and graft.

2. The method as claimed in claim 1, wherein said initial opening drilled to a depth just prior to reaching the hard floor of the sinus, is drilled to substantially 1 mm prior to reaching the hard floor of the sinus.

3. A kit for performing an inferior lift in a sinus within an initial opening in a bone including a marrow section and a hard sinus floor, said initial opening being drilled to a depth just prior to reaching said hard floor of said sinus, said kit comprising:

a first tip for a sonic drilling device, said first tip having an active portion that is substantially limited to a front region of said first tip said first tip configured to remove bone only in a forward direction of said first tip without substantially cutting contact with said marrow section of said bone, said first tip for removing a portion of said hard floor located within said initial opening until a schneiderian membrane is reached exposing said schneiderian membrane;

a second tip for said sonic drilling device, said second tip having an active portion that is substantially limited to 360 degrees about a circumference of a forward end of said second tip, said second tip configured to remove bone substantially in a lateral direction of said second tip without substantial cutting contact with said marrow section of said bone, said second tip for removing any remaining a small doughnut shaped hard sinus floor of said bone, clearing a widened opening in said hard sinus floor of said bone;

wherein said first and second tips for said sonic drilling device preparing said widened opening in said hard sinus floor of said bone sufficient to insert a bone graft into said widened opening, lifting said schneiderian membrane.

4. The kit as claimed in claim 3, wherein said initial opening drilled to a depth just prior to reaching the hard floor of the sinus, is drilled to substantially 1 mm prior to reaching the hard floor of the sinus.

\* \* \* \* \*